(12) United States Patent
Paulos

(10) Patent No.: US 8,657,880 B2
(45) Date of Patent: Feb. 25, 2014

(54) SURGICAL TENSIONING ASSEMBLY AND METHODS OF USE

(76) Inventor: Lonnie E. Paulos, Pensacola, FL (US)

( * ) Notice: Subject to any disclaimer, the term of this patent is extended or adjusted under 35 U.S.C. 154(b) by 373 days.

(21) Appl. No.: 12/937,388

(22) PCT Filed: Apr. 14, 2009

(86) PCT No.: PCT/US2009/040577
§ 371 (c)(1),
(2), (4) Date: Oct. 12, 2010

(87) PCT Pub. No.: WO2009/129269
PCT Pub. Date: Oct. 22, 2009

(65) Prior Publication Data
US 2011/0029079 A1 Feb. 3, 2011

Related U.S. Application Data

(60) Provisional application No. 61/045,095, filed on Apr. 15, 2008.

(51) Int. Cl.
*A61F 2/08* (2006.01)
*A61B 17/58* (2006.01)
*A61B 17/60* (2006.01)
*A61F 2/00* (2006.01)

(52) U.S. Cl.
USPC ........................................ 623/13.13; 606/88

(58) Field of Classification Search
USPC ............ 623/13.11–13.14; 606/86, 88, 96–98, 606/102–103 R, 139, 144–148, 86 R, 606/102–103
See application file for complete search history.

(56) References Cited

U.S. PATENT DOCUMENTS

| 4,950,271 A | 8/1990 | Lewis et al. |
| 5,037,426 A | 8/1991 | Goble et al. |
| 5,071,420 A | 12/1991 | Paulos et al. |

(Continued)

FOREIGN PATENT DOCUMENTS

WO WO2005102178 11/2005

OTHER PUBLICATIONS

Korean Intellectual Property Office, International Search Report (ISR) and Written Opinion (WO) of the International Searching Authority for related PCT App. No. PCT/US2009/040577, filed Apr. 14, 2009, ISR and WO Mailed Oct. 30, 2009, Korea.

(Continued)

*Primary Examiner* — Andrew Yang
*Assistant Examiner* — Diana S Jones
(74) *Attorney, Agent, or Firm* — John Brooks Law LLC; John J. Brooks, III

(57) ABSTRACT

A surgical tensioning assembly providing a means to apply a variable and selective force to tissues, such as replacement ligaments, during a ligament reconstruction surgery. The assembly provides a means to apply a selective, measurable and a generally balanced force on multiple tissues. One embodiment of the tensioning assembly includes a set of subassemblies, namely an engagement subassembly, a variable force subassembly and an equalizing subassembly. These subassemblies are operably connected to each other such that they are able to provide tension on tissues connected to the assembly. In one embodiment the tensioning assembly further includes a mounting subassembly that provides a means to connect the tensioning assembly to a person's body. Methods of use of the surgical tensioning assembly are also disclosed to include novel methods of cycling and conditioning tissue used in a knee ligament replacement surgery.

24 Claims, 8 Drawing Sheets

(56) References Cited

U.S. PATENT DOCUMENTS

| | | |
|---|---|---|
| 5,108,433 A | 4/1992 | May et al. |
| 5,713,897 A | 2/1998 | Goble et al. |
| 6,001,106 A | 12/1999 | Ryan et al. |
| 6,679,889 B1 * | 1/2004 | West et al. ............ 606/88 |
| 2003/0176920 A1 | 9/2003 | Sklar et al. |
| 2004/0039389 A1 | 2/2004 | West, Jr. et al. |
| 2008/0033549 A1 * | 2/2008 | Marshall et al. ........... 623/13.13 |

OTHER PUBLICATIONS

International Bureau of the WIPO, International Preliminary Report of Patentability (IPRP) for related PCT App. No. PCT/US2009/040577, filed Apr. 14, 2009, IPRP Issued Oct. 19, 2010, Switzerland.

* cited by examiner

SURGICAL TENSIONING ASSEMBLY AND METHODS OF USE

CROSS-REFERENCE TO RELATED APPLICATIONS

This application claims the benefit of U.S. App. No. 61/045,095, filed on Apr. 15, 2008, entitled "LIGAMENT TENSIONING ASSEMBLY AND METHODS OF USE," the entire content of which is incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention is in the field of joint repair surgery, such as reconstruction of the anterior cruciate ligament (ACL). More particularly, the invention is in the field of tensioning devices for conditioning and pre-tensioning multiple tissue grafts used in joint repair procedures. The invention is able to independently condition and pre-tension each tissue graft individually.

2. Description of the Related Art

Recent studies have added to the understanding of graft tension by demonstrating that unequal tension in the individual strands of the tissue graft can result in significant losses in total graft strength and stiffness. Unequal conditioning of each of a multiple of tissue grafts, can lead to uneven loads being borne by each individual graft. Regardless of the causes for unequal application of material stress to each of the individual tissue grafts, the "tighter" graft (or graft with higher material stress) will reach the failure point first, thereby causing a lower load to failure for the composite graft.

While much of the focus has been directed to the issue of under tensioning, which typically results in knees that are less stable than normal, application of too much tension may in theory also have an adverse effect by constraining the joints or causing increased pressure on articular surfaces.

There are several ligament tensioning devices presently available on the market. Additionally, U.S. Pat. No. 6,679,889 to West entitled "Apparatus and methods for independently conditioning and pretensioning a plurality of ligament grafts during joint repair surgery" (#889) which is herein incorporated in its entirety. A predetermined amount of stress is applied to the tissue grafts in order to provide a reconstructed joint that has a desired amount of stability and stiffness. Inadequately tensioned tissue grafts often yield a joint that is not adequately stable or a joint that is too loose and more prone to subsequent injury and possible rupture of the tissue grafts. However, unless each strand of a multiple strand graft bears approximately the same magnitude of material stress, the strand that initially bears the highest material stress will reach the failure point and rupture first when the joint is subjected to high stress. Subsequently, the graft initially bearing less material stress will then bear all the stress and be more prone to failure since it will be acting on its own to hold the joint together.

Embodiments of the present tensioning assembly provide features that address shortcomings present in tensioning assemblies known on the market today.

SUMMARY OF THE INVENTION

Embodiments of the present invention include a novel apparatus and methods to solve the problems associated with the inability to condition and pre-tension each strand of a multiple-strand tissue graft. The tensioning devices according to the present invention may be configured to apply a desired amount of tension or load to single-stranded or multi-stranded grafts.

It is an object of one embodiment of the invention to provide a surgical tensioning assembly comprising an engagement subassembly having at least a first and second engagement element to engage at least two ligament arms, a means to vary a force applied to the at least two ligament arms through the engagement subassembly, and a means to automatically balance the force applied to the at least two ligament arms so that when the at least two arms are engaged by the engagement elements, the force applied to the at least two ligament arms is balanced.

It is another object of one embodiment of the invention to provide a surgical tensioning assembly wherein the means to balance the force comprises an equalizing subassembly operably connected to the means to very a force so that the force applied to the at least two ligament arms is about equal.

It is yet another object of one embodiment of the invention to provide a surgical tensioning assembly wherein the equalizing subassembly comprises a rocker arm operably connected to the means to vary the force.

It is a further object of one embodiment of the invention to provide a surgical tensioning assembly wherein the at least two ligament arms are connected to at least one suture and the first and second engagement element comprises a first and second rotatable wheel configured to receive and retain the sutures when they are connected and looped around the wheel.

It is an object of one embodiment of the invention to provide a surgical tensioning assembly further comprising a mounting subassembly to removably attach the tensioning assembly to a patient's body, the mounting subassembly having at least one stabilization leg to slidably attach to a guide pin affixed to the person's body so that the tensioning assembly can be attached and detached from the patient's body.

It is another object of one embodiment of the invention to provide a surgical tensioning assembly wherein the equalizing subassembly comprises a rocker arm operably connected to the means to vary a force so that the force applied to the at least two ligament arms is about equal, the at least two ligament arms are connected to at least one suture, the engagement element comprises a rotatable wheel configured to receive and retain the at least one suture when the sutures are connected and looped around the wheel, and the means to vary the force further comprises a first and second variable force subassembly configured to apply and transfer a first and second selective force to the first and second engagement elements.

It is an object of one embodiment of the invention to provide a surgical tensioning assembly comprising an engagement subassembly having a first and second engagement element capable of engaging at least two tissue arms, a variable force subassembly configured to engage and apply at least one selective force to the first and second engagement elements and an equalizing subassembly operably connected to the variable force subassembly so that when the at least two tissue arms are engaged by the first and second engagement elements the force applied to the at least two tissue arms is about equal.

It is another object of one embodiment of the invention to provide a surgical tensioning assembly wherein the variable force subassembly comprises one force element.

It is a further object of one embodiment of the invention to provide a surgical tensioning assembly wherein the equalizing subassembly further comprises the rocker arm having a first and second end, a rocker mount, and a guide pin pivotally connecting the rocker mount to the rocker arm whereby a force on the first and second end of the rocker arm can be balanced.

It is another object of one embodiment of the invention to provide a surgical tensioning assembly comprising an engagement subassembly having a first and second engagement element capable of engaging at least two tissue arms, a variable force subassembly configured to engage and apply at least one selective force to the first and second engagement elements, and an equalizing subassembly operably connected to the variable force subassembly about a pivot point such that when the at least two tissue arms are engaged by the first and second engagement elements the force applied to the at least two tissue arms is balanced about the pivot point.

It is another object of one embodiment of the invention to provide a method for tensioning a multi-stranded tissue graft during joint repair surgery comprising the steps of affixing a surgical tensioning assembly to a patient's body, ensuring a first end of at least one tissue arm is secured in the patient's body, engaging a second end of the at least one ligament arms with a first and second engagement element of the tensioning assembly, applying a variable force to the first and second engagement element, and automatically equalizing the variable force between the first and second engagement element so that when at least one ligament arm is engaged by the first and second engagement element, the force applied by the engagement elements to the at least one arm is balanced.

It is yet another object of one embodiment of the invention to provide a method for tensioning a multi-stranded tissue graft during joint repair surgery wherein the method is used for tensioning a ligament during a ligament reconstruction of a patient's knee.

It is a further object of one embodiment of the invention to provide a method for tensioning a multi-stranded tissue graft during joint repair surgery wherein the method further comprises conditioning the ligament by cycling the patient's knee, measuring the variable force through the cycling and varying the variable force until a difference in the variable force does not exceed a difference of 10 percent and securing the second end of the ligament to the patient's knee.

BRIEF DESCRIPTION OF THE SEVERAL VIEWS OF THE DRAWINGS

A more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
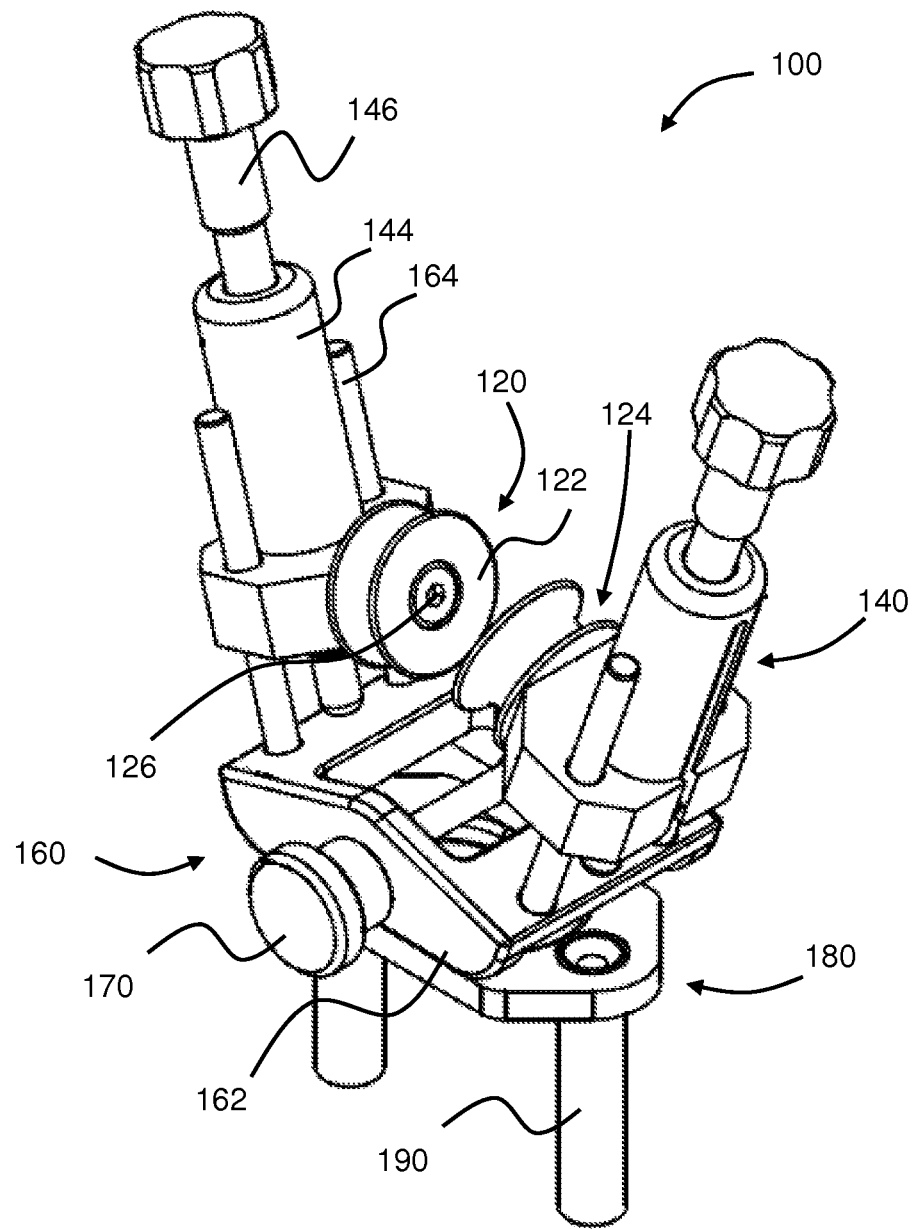
FIG. 1 is a top perspective view of one embodiment of the tensioning assembly.

The present invention is directed to an apparatus and methods for independently tensioning a plurality of tissue grafts during surgical procedures, such as in procedures to replace the anterior cruciate ligament (ACL) or the posterior cruciate ligament (PCL). In order for the tissue graft to provide adequate joint stability and provide a predetermined amount of strength, but due to the tendency of many soft tissue grafts (e.g., ACL replacement) and/or sutures attached thereto to relax after the graft has been implanted, it is often necessary or desirable to pre-stress (or pre-tension) the graft prior to permanently anchoring them to the bone. The proper pre-tensioning of the tissue graft can provide a predetermined amount of joint stability and strength and can help to ensure the success of the surgical procedure.

Where multiple strands of tissue are used as the ligament graft, or multiple arms of a single graft are used, it is often difficult using prior-art devices and procedures to ensure equal, or substantially equal, conditioning and pre-tensioning of each strand. Unless each ligament graft is pre-tensioned properly, it is unlikely that each of the soft tissue strands will contribute equally to the strength of the joint. It is possible that the strands or arms that have not been adequately pre-tensioned may bear little, if any, of the load applied to the joint during normal use, absent stretching or tearing of the more highly conditioned and pre-tensioned strands. In the case of grafts comprising a pair of strands or arms, one of which is improperly pre-tensioned, the majority of the load will be born by the strand that has carries the most tensile force.

A surgical tensioning assembly and methods for use will now be described in detail. Although embodiments are described for use with human knee ligaments, it is understood that the methods and systems described can be for use in other similar medical procedures with similar soft tissues. Notwithstanding the specific example embodiments set forth below, all such variations and modifications that would be envisioned by one of ordinary skill in the art are intended to fall within the scope of this disclosure.

In one embodiment, the surgical tensioning assembly provides a means to apply a varied and selective force to ligaments, or replacement ligaments, during a ligament reconstruction surgery. The assembly provides a means to apply a selective and measurable force and in some embodiments the force can be altered and in embodiments the force can be balanced or equalized between multiple ligaments.

This surgical tensioning assembly allows a surgeon to place the ligament under tension prior to fixation and allows them to observe the behavior of the new ligament as the knee is taken through a range of motion. This assembly and method builds safety into the procedure so that the ligament is not over tensioned and the knee entrapped, creating subsequent motion problems and/or arthritis.

One Embodiment of the Surgical Tensioning Assembly:

One embodiment of the surgical tensioning assembly is shown in FIG. 1. As shown, the surgical tensioning assembly 100 comprises a set of substructures or subassemblies, namely an engagement subassembly 120, a variable force subassembly 140 and an equalizing subassembly 160. In the embodiment shown in FIG. 1, the tensioning assembly further includes a mounting subassembly 190 that provides a means to connect the tensioning assembly to a person's body. These subassemblies are operably connected to each other such that they are able to provide tension on tissues connected to the assembly.

Referring to FIG. 1, the engagement subassembly 120 provides a means for the assembly to engage multiple sutures and generally provides at least one engagement element to receive sutures. The variable force subassembly 140 provides a means to vary the force on sutures engaged with the tensioning assembly 100 and the patient's body. Generally, the variable force subassembly 140 comprises a force element that is able to put a force on other assembly elements. The equalizing subassembly 160 provides a means to equalize the force applied by the variable force subassembly 140 on the sutures or tissue grafts and generally provides at least one rocker element to equalize the forces applied to the sutures or tissue grafts. A mounting subassembly 190 provides a means to mount the tensioning assembly 100 to a patient's body.

Figure 2A:
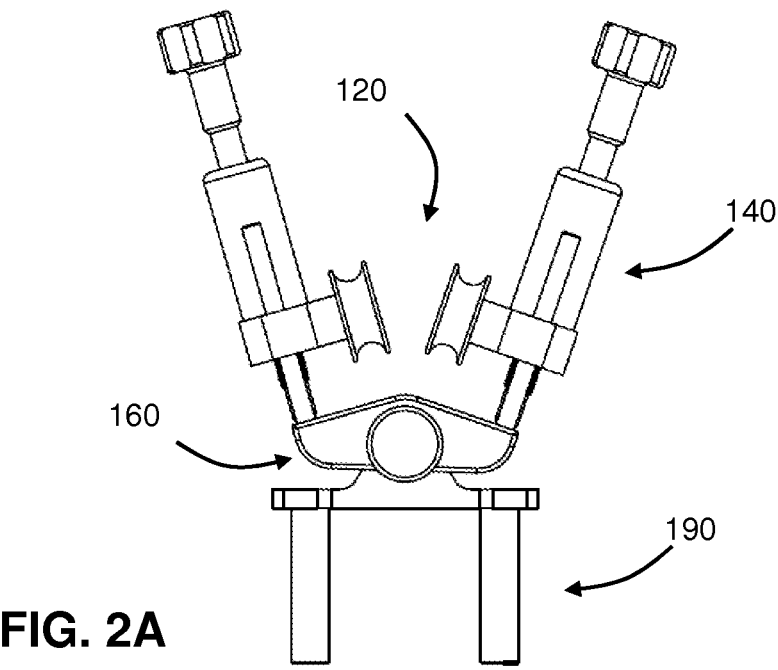
FIG. 2A is a front view of one embodiment of the tensioning assembly.
Figure 2B:
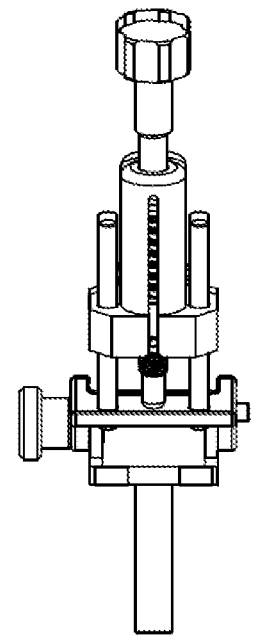
FIG. 2B is a side view of one embodiment of the tensioning assembly.

FIG. 2A shows a front view of one embodiment of the assembly and FIG. 2B shows a side view of one embodiment of the assembly. FIG. 2A shows the engagement subassembly 120, the variable force subassembly 140, the equalizing subassembly 160 and the mounting subassembly 190.

One Embodiment of the Engagement Subassembly:

Generally, the engagement subassembly provides at least one engagement element to engage tissue arms as well as structural elements to integrate with the rest of the assembly. As used throughout this description, engage means to interlock, attach, hold, receive or to otherwise connect one body with another in a manner that allows a force to be transferred between the bodies. Particularly, in embodiments of the present assembly, engagement with the engagement elements means to removably attach or receive tissue arms (or elements connected to the tissue arms) with the engagement elements so that forces can be transferred between the elements and the tissue arms.

In the embodiment shown in FIG. 1, the engagement element 122 comprises a rotatable wheel with a circumferential channel 124 and a central connection element 126 such as a shoulder bolt allowing the wheel to freely rotate about its central axis when connected to another element of the assembly 100. The channel 124 allows a suture loop to be placed and retained in the channel 124 while a force is applied to either or both ends of the suture. The central connection element 126 operably connects the engagement element 122 to the variable force assembly 140 which in turn is operably connected to the equalizing subassembly 160. In this embodiment, the connection between the engagement subassembly 120 and the variable force subassembly 140 is by having portions of the engagement subassembly being cooperatively received by the slide block element 144 of the variable force assembly 140. The connection between the engagement subassembly 120 and the equalizing subassembly 160 can be a direct connection or an indirect connection.

Although the engagement element 122 is a pulley-like rotatable wheel in this embodiment, other embodiments of an engagement element are contemplated such as simple hooks, magnets, non-rotatable elements, balancing elements or rocking elements that can be used to balance at least two forces engaged with the element or any combination thereof. It is also contemplated that direct connections to the sutures or the grafts can be utilized in embodiments. These other embodiments can include, but are not limited to direct clips, hooks, screws, buttons or other methods of engaging a tissue with the assembly.

Figure 4:
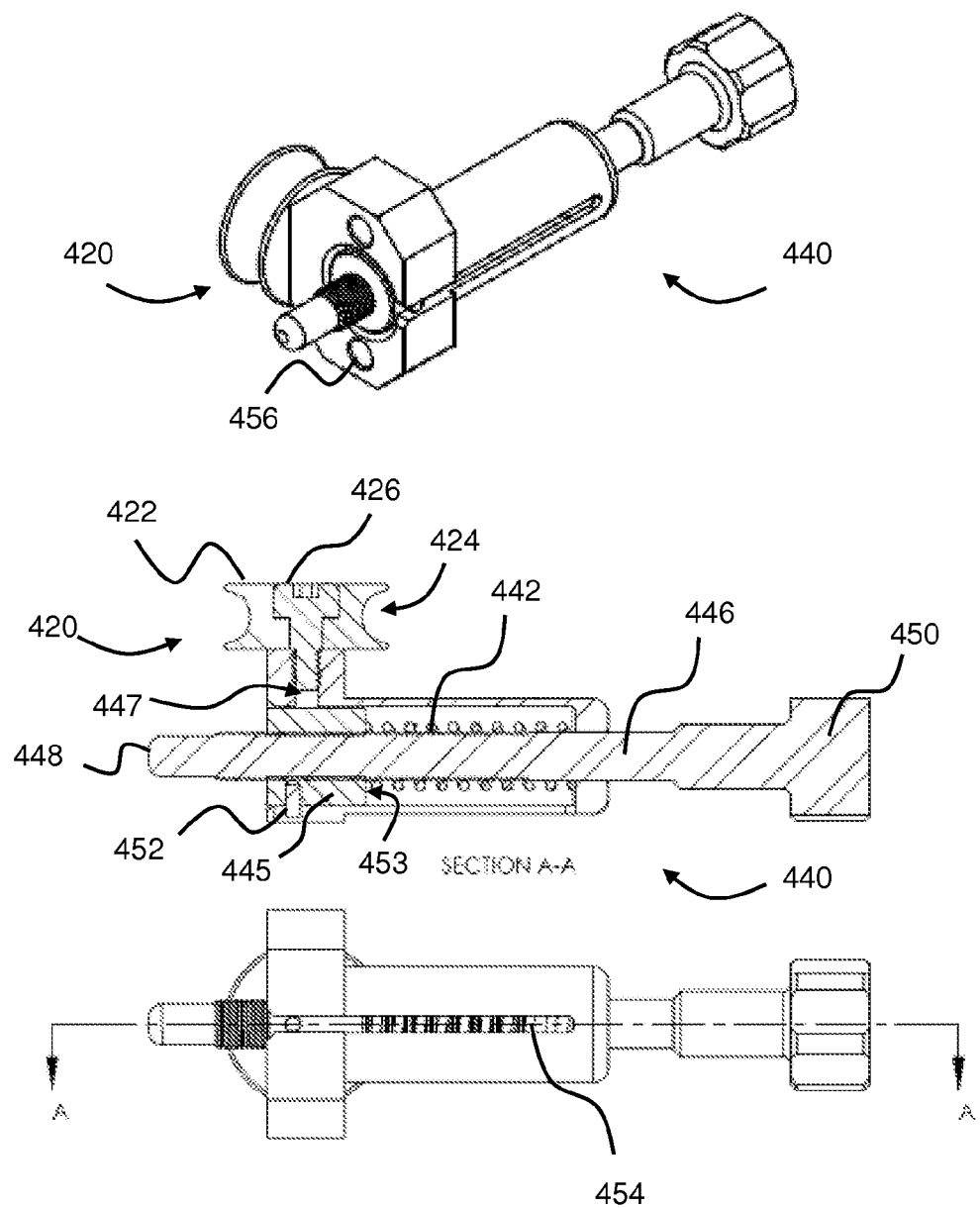
FIG. 4 includes multiple views of one embodiment of the variable force subassembly for one embodiment of the tensioning assembly.

In order to better understand the mechanical structures and operation of the engagement subassembly, more particular reference is made to one embodiment in FIG. 4. In the embodiment shown in FIG. 4, the engagement subassembly 420 comprises the engagement element 422 configured to receive and retain the sutures when they are looped around the element 422 and in the circumferential channel 424. The central connection element 426 is a shoulder bolt with a threaded end to be received in a mating threaded recess 447 in the variable force subassembly 440. The shoulder bolt 426 retains the element 422 and allows the element 422 to rotate freely.

One Embodiment of the Variable Force Subassembly:

Generally, the variable force subassembly includes a force element that is able to put a force on other assembly elements. In the embodiment shown in FIG. 1, the variable force subassembly 140 comprises a force element retained within the hollow of the slide block 144. The slide block also connects the variable force subassembly to the engagement subassembly 120. In the embodiment shown, the slide block 144 is generally hollow and retains the force element (not shown) which can be, but is not limited to a resilient or compressible element such as a spring. The subassembly 140 also has an adjustment element 146 that allows the subassembly to move relative to the rest of the assembly. This movement allows the subassembly 140 to be properly positioned during surgery as well as provide a method of varying the force applied by the force element when the assembly is engaged with a tissue or sutures.

In order to better understand the mechanical structures and operation of the variable force subassembly, more particular reference is made to one embodiment shown in FIG. 4. In the embodiment shown in FIG. 4, the variable force subassembly 440 comprises a slide block 444, a force element 442, a force nut 445, and an adjustment element 446. In the embodiment shown, the slide block 444 comprises an element with a generally hollow space extending from its proximal to distal ends. The adjustment element 446 is an element that allows the user to adjust the force put on the engagement elements. In FIG. 4, the adjustment element 446 comprises a threaded bolt having threads on its distal end 448 that mate with inner threads in the force nut 445. The adjustment element's proximal end 450 includes a knob that is knurled or otherwise shaped for easy turning by the hands of the user. When the adjustment element is turned by turning the proximal end 450, the threads engage the force nut 445 and urge the nut to move up or down the adjustment element 446. This in turn, moves the force nut surface 453 on which the force element rests which also translates that force on the slide block 444. When there are no other forces on the slide block 444, this will typically allow the slide block 444 to move up and down the adjustment element 446 also. If there are other forces on the slide block 444, such as may be exerted by the engagement subassembly 420, the movement of the force nut 445 alters that force depending on the direction of both forces. Through this interaction, the turning of the adjustment element 446 can simply move the other elements of the variable force subassembly 440 or it can vary the force exerted by the subassembly onto the engagement subassembly 420. In embodiments, the variable force subassembly 440 exerts force onto the engagement subassembly 420 which is connected to the slide block 444 by a matingly threaded recess 447 receiving the connection element 426.

In addition to being able to vary the force applied by the variable force subassembly 440, embodiments of the variable force subassembly 440 allow the force applied by the force element 442 to be measured and therefore selected through the use of calibrated force elements and a measurement element 452. In the embodiment of FIG. 4, the measuring element 452 comprises a nub that is connected to the force nut 445. The force element 442, such as a spring, has a known resistance to force so that a certain compression of the spring represents a certain amount of resistance force. The measuring element 452 moves up and down a slot 454 with calibration markings on the outside of slide block that correspond to compression force values for that force element 442 when it is compressed to known points between the force nut surface 453 and the proximal end of the slide block 444. The calibration markings may provide any desired measuring standard, such as metric (e.g., Newtons) or English units (e.g., pounds), as well as any desired level of precision.

In the embodiments shown in FIGS. 1, 2A and 2B, the embodiments comprise two variable force subassemblies. It is understood and contemplated that other embodiments are possible with one or more than two of these subassemblies.

Although the above description and illustrations discuss a force element and measurement elements such as a calibrated spring, it is understood that many other force and measurement element embodiments are possible. Examples of contemplated calibrated force elements include, but are not limited to a variety of simple scales, such as tension springs, compression springs, torsion springs, magnets, stress sensors or elastomeric materials. In addition a variety of electronically actuated and measured force elements are within the scope of the invention so long as they are capable of independently applying a force to on assembly elements and making the user aware of the force being exerted on the assembly elements.

One embodiment of the Equalizing Subassembly:

The equalizing subassembly provides a means to balance the force applied by the variable force subassembly onto the sutures. Generally, this subassembly provides a floating platform, or at least one rocker element to balance the forces applied to the sutures. Balance as used herein includes equalizing as well as taking into account the force and the distance that force is applied about a point such as a pivot point. As shown in the embodiment in FIG. 1, the equalizing subassembly comprises a rocker arm 162, having a plurality of guide rails 164, a guide pin 170 and a rocker mount 180. The equalizing subassembly balances the forces that are put on the tensioning assembly by elements such as sutures engaged with the engagement elements. In this embodiment, the elements of the equalizing subassembly 160 are positioned such that they balance the forces put onto sutures by the two engagement subassemblies 120.

Figure 3:
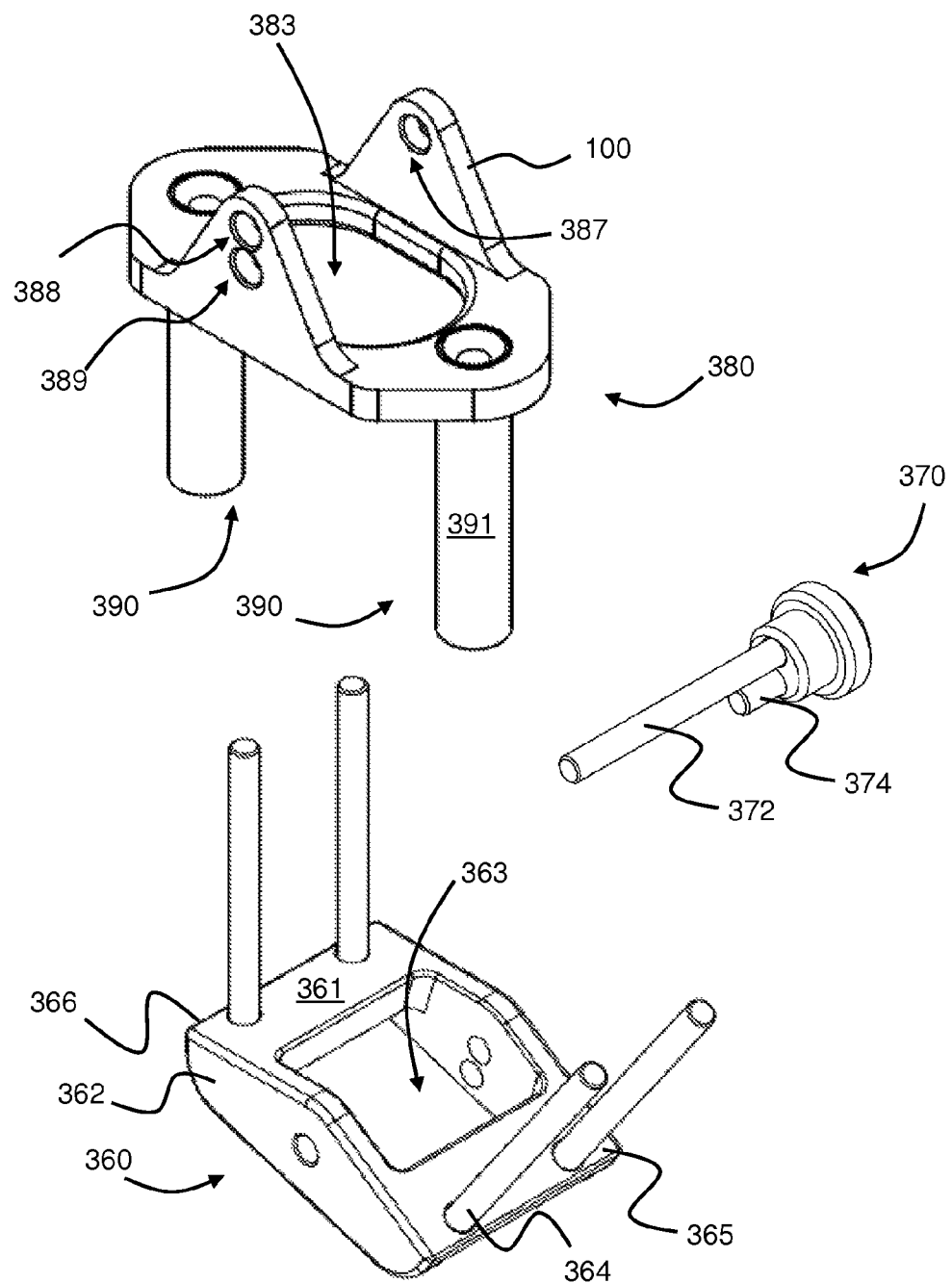
FIG. 3 includes views of embodiments of some components of the equalizing assembly for one embodiment of the tensioning assembly.

In order to better understand the mechanical structures and operation of the equalizing subassembly, more particular reference is made to one embodiment in FIG. 3. In the embodiment shown in FIG. 3, the equalizing force subassembly comprises a rocker arm 362 having multiple guide rails 364, a guide pin 370 and a rocker mount 380. The guide rails 364 removably connect and guide the slide block of the variable force subassembly. As shown, the guide rails 364 are elongaged rods connected to a first end 366 and second end 365 of the rocker arm 362. The rods are sized to be slidable within through holes 456 (shown in FIG. 4) at the distal end of the slide block.

Although not required, this embodiment has a curved rocker surface 361 so that when the guide rails 364 are connected perpendicular to a point in the surface 361, the rails are at a diverging angle relative to each other. The curve of the surface 361 and the diverging angle can also be helpful to allow the surgeon to engage the sutures with the assembly. The curve and angle can also be helpful when the sutures and grafts are coming from multiple tunnels in a ligament reconstruction surgery and the angle reflects the angle of the tunnels and reduces the friction the sutures may have on the side of the tunnel.

The guide rails 364 provide the means to connect the equalizing subassembly to the variable force subassembly. In this embodiment, the means to connect comprises a pair of two elongated rods 364 extending in a direction perpendicular to the surface 361 of the rocker arm 362 within the two-dimensional plane in which the rocker rocks. The guide rails 364 allow the variable force assembly to freely slide up and down the rails without rotating or rotating. The guide rails 364 are also long enough to provide room for the surgeon to adjust the variable force subassembly with the adjustment element. The guide rails 364 can also be shaped to allow the variable force subassembly to be removed and replaced so that the engagement elements can be placed either towards each other, towards the center of the assembly or opposite each other and on the outside of the assembly. Other methods of connecting the equalizing subassembly to the variable force subassembly are contemplated such as but not limited to clips, slides, wheels, channels, rollers or hooks, on either of the subassemblies, that mate with the other subassembly and allow the forces on the engagement elements to be balanced.

In the embodiment of FIG. 1, the guide pin 170 and the guide pin holes (not shown) provide a hinged or pivoted attachment between the rocker arm 162 and the rocker mount 180 whereby the rocker arm 162 can freely balance the two ends of the rocker arm. As shown in FIG. 1, the two attachment points with the variable force subassembly are at opposing first and second ends of the rocker arm 162 and the hinged connection is generally at the middle of the rocker arm. When connected with the rocker mount 180 through the use of a guide pin 170, the equalizing subassembly 160 allows the two variable force subassemblies 140, which are operationally attached to the engagement subassemblies 120, to freely rock or pivot about the connection. In this embodiment, with the guide pin generally in the middle of the two force subassemblies, the forces applied by the two subassemblies onto the equalizing subassembly is about equally balanced. FIG. 3 illustrates details of one embodiment of the guide pin 370 with a through pin 372, a locking pin 374 and the rocker mount 380 having through pin holes 367 and 368, and locking hole 369.

In the embodiments shown in FIG. 3, the rocker arm 362 also has centralized gap 363 that corresponds with a centralized gap 383 in the rocker mount 380. These centralized gaps provide a channel through which sutures can pass from the bottom side of the assembly up to and engage the engagement elements. These centralized gaps are included in this embodiment because of the location of the engagement elements. It is understood that many other means of allowing the tissue or sutures to engage the engagement elements is within the embodiment contemplated within this disclosure.

It is understood that other embodiments of the equalizing subassemblies can balance forces on the engagement elements. These other embodiments include, but are not limited to, a platform that freely floats multidirectionally on a bed of bearings or magnets, a combination of pulleys or hinges that can balance forces or any other means of balancing at least two forces put on the assembly.

One Embodiment of the Mounting Subassembly and Other Elements:

In the embodiment of FIG. 1, the mounting subassembly 190 connects to the rocker mount 180 and provides the ability to stabilize and properly place the assembly on the patient's bone. In the embodiment shown, the mounting subassembly 190 comprises two stabilization legs to slidably receive elements such as mounting pins that are rigidly attached to a patient's bone. One embodiment of the mounting subassembly is shown in more detail in FIG. 3 comprising multiple hollow stabilization legs 391 that receive a mounting pin, such as a typical surgical guide pin in one end while the other end is connected to the rocker mount 380. In some embodiments, the pins are shouldered pins that are received up to a point in the stabilization legs where the diameter of the hollow part of the leg cannot proceed beyond the shoulder.

One of ordinary skill in the art, in light of the teachings herein, will readily appreciate that virtually any desired mechanical mating mounting system may be employed as a mounting assembly so long as it provides for selective attachment and detachment of the tensioning assembly from the surgical site. Other mounting subassemblies are contemplated such as but not limited to belts, rings, magnets, braces or tools that provide a rigid connection between the surgical location and the tensioning assembly.

The tensioning assembly can also operate with a drill template to locate the positioning holes for the mounting pin. The drill template has predetermined pin holes that correspond to the location of the end of the mounting system stabilization legs such that when pins are placed in the bone at these pin holes, the ends of mounting pins are located so that they can be slidably received by the mounting subassembly. The drill template can either be visually placed by the surgeon or it can also include a reference point that may interact with one or more reference points in or near the patient's surgical location such as a bone tunnel.

Embodiments of the surgical tensioning assembly may also include sutures and well known elements to tie or connect sutures to tissue strands.

One embodiment of the assembly is used in ligament repair procedures with other devices such as, but not limited to, a cannulated ligament guide, pins, guide wires, ligament guide, a trephine system, a fixation device, woven sutures, and pulleys.

Figure 5:
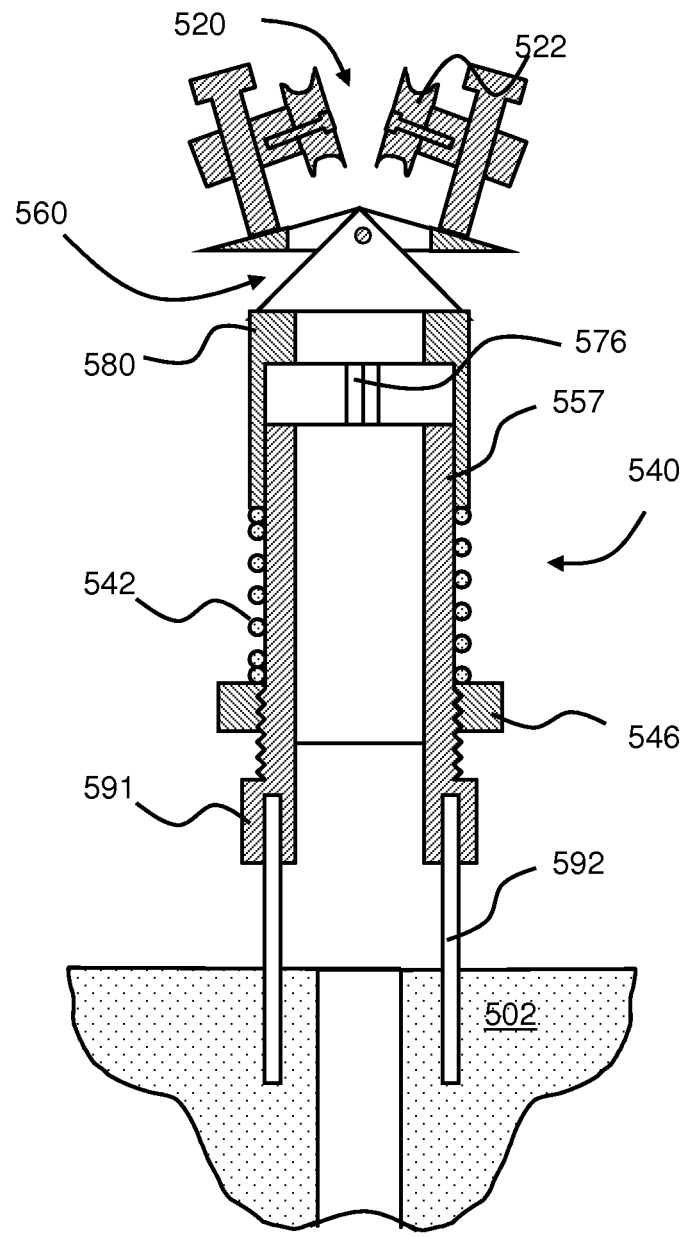
FIG. 5 is a side cut-away view of one embodiment of the tensioning assembly with one variable force subassembly.

Other Embodiments of the Tensioning Assembly:

An alternative embodiment of the assembly is shown in FIG. 5. In this embodiment, the variable force is provided by a single variable force subassembly 540 with a single force element 542. The variable force subassembly 540 provides a measurable force on the engagement elements 522 relative to the mounting subassembly and still allows the forces on the engagement elements 522 to be balanced by the equalizing subassembly 560.

As shown, the stabilization legs 591 are placed on the mounting pins 592 that are affixed to a patient's bone 502. The variable force subassembly 540 provides a force onto the equalizing subassembly 560 which in turn provides a force onto the engagement subassembly 520. The connection of the variable force subassembly 540 to the equalizing subassembly 560 is through a compressible slipping connection that includes a calibrated force elements such as a spring 542. The variable force subassembly 540 comprises an inner cylinder 557 within the calibrated spring that slides relative to the rocker mount 580. The rocker mount optionally has a guide rail 576 that cooperates with a slot in the inner cylinder to prevent twisting of elements relative to each other. In this embodiment, a force put onto the equalizing subassembly 560 compresses the calibrated spring 542 and the spring compression is translated to a measurable force through measurement embodiments similar to those described herein. In the embodiment of FIG. 5, the variable force subassembly 540 is attached to the equalizing subassembly 560 which balances the engagement elements 522. The connection of the equalizing subassembly 560 is such that it provides a concentrated point of force that is translated to the force element 542 and the engagement element 522. The connection also allows the engagement elements 522 to pivot and equalize the force put on each of them. This embodiment allows the single force element 542 to be adjusted by an adjustment element 546 embodiment that comprises a threaded ring that cooperates with threads on the inner cylinder 557 such that turning the ring provides the adjustment features for the variable force element described herein. As shown, turning the adjustment element 546 raises or lowers the adjustment element 546 on the cylinder 557 which in turn increases or decreases the force put on the force element 542. As with other embodiments, it is possible to have a calibrated force element that measures the force applied to the engagement elements. The force applied by the force element 542 should be equal for each of the tissues engaged with the assembly. The operation of the engagement elements also equalizes the force put on sutures that are looped around them. The result is a floating and compressible connection that equalizes and measures the forces put on the sutures looped around the engagement elements.

It is understood that there are other embodiments similar to the one shown in FIG. 5 where the variable force assembly comprises a single subassembly that cooperates with the assembly elements to vary and measure the forces put on the suture elements and sutures. In particular, it is also contemplated that the means of varying and measuring the force put on the ligaments is provided through other embodiments. These other embodiments include, but are not limited to calibrated elements that measure force applied to the force balancing elements or calibrated elements that measure force applied to the equalizing subassembly or other assembly components.

It is also understood that embodiments of the tensioning assembly can be used and configured for multi-tunnel procedures with diverging tunnels such as may be used on a femur for a double-bundle ACL reconstruction. For this procedure, the tunnel locations, and therefore the position of the sutures can be spread at a distance. The distance and angle of the tunnels can make equalizing the tension on ligament arms difficult. With one embodiment of this tensioning assembly, this situation can be accommodated with an embodiment similar to that shown in FIG. 1 having a large gap in the rocker arm and rocker mount or it could be accommodated by flipping the position of the engagement elements to the outside of the assembly. Either of these embodiments will allow the sutures to more freely move within the tunnel with less frictional engagement of the tunnel walls. It is understood that these embodiments may require adjustments to the configuration of the assembly such as but not limited to the location of the stabilization legs.

It is understood that embodiments of the equalizing subassembly may be configured to balance the forces being applied to the equalizing subassembly, but these forces may not be equal and may represent different forces engagement elements and the variable force subassemblies. For example, and not for limitation, rather than having the variable force subassemblies mounted at an equal distance from the pivot point of the guide pin as shown in FIG. 1, if the variable force subassemblies were mounted at different distances from the pivot point, the equalizing subassembly can function to balance different forces on the variable force subassemblies. The balancing proportions can be predetermined by predefining the points on the rocker arms where the force of the engagement elements are transferred to the equalizing subassembly. By predefining these points and recognizing the leverage caused by forces at set distances from the pivot point, a predetermined proportional relationship of forces on the engagement elements can be balanced. For example, using the embodiment of FIG. 1, if one variable force subassembly was placed at a distance twice as far from the guide pin as the other, the equalizing subassembly would balance a force of a 1× magnitude on that distant engagement element with a force of 2× on the other engagement element. By using common principals of physics and simple machines, it is understood that any proportional relationship can be obtained by varying the distance from the pivot point.

It is also understood that in some embodiments of methods of ligament reconstruction, tissue strands may have different dimensions, such as different diameters, and applying a standard, balanced load may result in different material stresses per strand dimension. Therefore, to accommodate differences in strand properties and for other reasons, it is contemplated that the tensioning assembly can be configured to allow for variable positioning of the variable force elements on the equalization subassembly so that the forces on the strands can be proportional to the strand properties. An example of this feature includes a movable mount for the variable force subassembly that moves the subassembly toward and away from the pivot point (guide pin) as desired. With this example, a relational chart could be used that would have the proportional properties of the tissues strands that could be measured by the surgeon, and the chart would have relative positions of the variable force subassemblies. The tensioning assembly could also have calibration markings on the assembly to guide the surgeon's positioning of the variable force subassemblies as directed by the relational chart.

It is also understood that embodiments of the tensioning assembly can potentially be used to monitor isometry and measure tension in a single or double strand of a tissue graft.

It is also understood that the embodiments of the tensioning assembly can utilize force elements that provide force by tension or other resilient means in addition to compression means.

One Embodiment of the Surgical Tensioning Assembly in Operation:

Embodiments of the methods herein provide for the automatic equalization of tension provided by the disclosed tensioning assembly. Therefore, although an embodiment of a ligament tensioning assembly as shown in FIG. 1 will be described as used in a double-bundle ACL reconstruction procedure and particularly for a tibial tunnel, it is understood that this description is for illustration purposes and not for limitation. The methods disclosed are also applicable to femoral tunnels for ACL reconstructions as well as other procedures such as PCL reconstruction and are expected to have broader applicability in other surgical procedures.

As described above, with the embodiment shown in FIG. 1, the engagement elements comprise two engagement elements, such as pulleys, shaped to receive sutures attached to arms of strands of a tissue graft. In this embodiment, the sutures comprise two sutures each from two ligament arms and each suture will be looped around the pulley. The engagement elements equalize the force put on both of the ligament arms attached to the suture, or sutures. The cooperation of the equalizing subassembly and the two engagement elements of this embodiment, allow the force to be balanced on all of the sutures and ligament arms.

Figure 6:
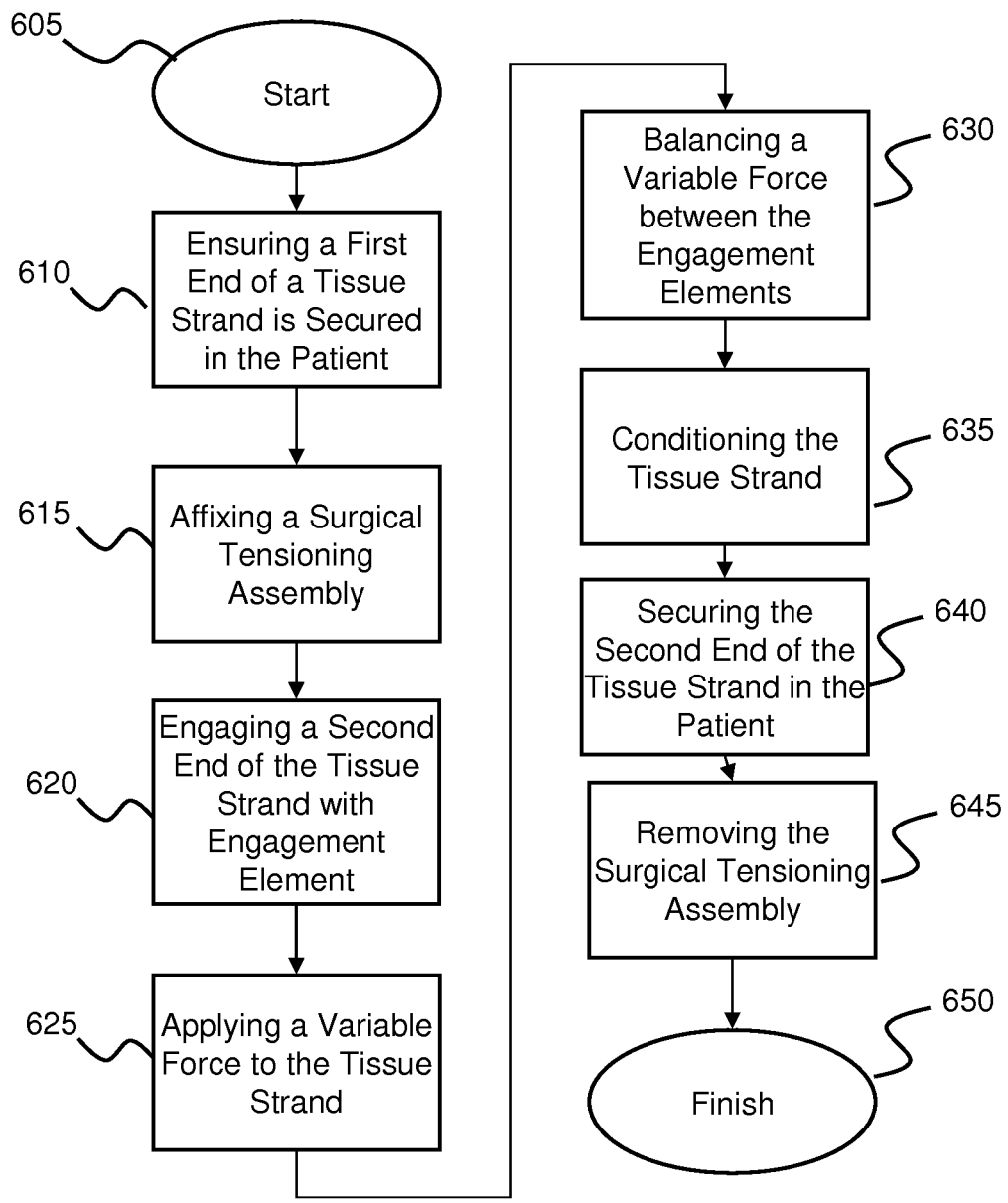
FIG. 6 is a process diagram of one embodiment of the methods of the invention.

One embodiment of a method of the present invention is shown in FIG. 6. The methods are used with common surgical procedures that involve a surgeon inserting inserting arthroscopic surgical instruments, or the like, through portals formed in the areas of the knee between the distal femur and proximal tibial surfaces. The methods disclosed also include the normal preoperative procedures to include diagnosis, preparation of the surgical site and provision of instruments common in ligament reconstruction procedures. The patient is typically in a position that provide good access to all aspects of the knee and the knee can be easily flexed about 100 degrees.

Figure 7:
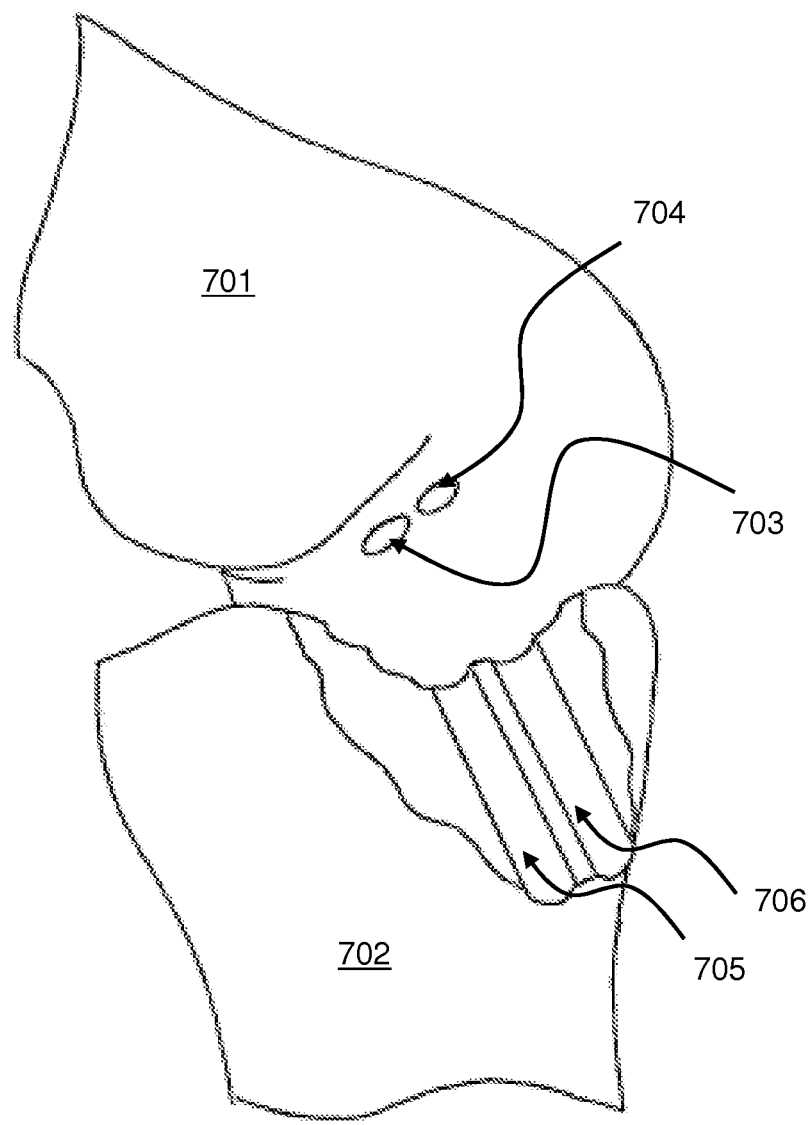
FIG. 7 is a side perspective view of a knee prepared for one embodiment of a double bundle ACL reconstruction procedure, the figure showing a cut-away of the tibia illustrating the tibial tunnels.

Typically, prior to the use of the tensioning assembly, one or more tunnels are bored through each of the bones comprising the joint. These tunnels are used to secure the tissue graft to the bones constituting the joint. In the case of a double bundle reconstruction of the ACL, as shown in FIG. 7, tunnels 703 and 704 are bored through the femur 701 and corresponding tunnels 705 and 706 are bored through the tibia 702 using known surgical procedures. Examples of common tunnel procedures include double tunnel procedures such as those disclosed in U.S. Patent Pub. No. US 2006/0271059 A1 to Clive Reay-Young et. al. entitled "Convergent tunnel guide apparatus and method" which is herein incorporated by reference in its entirety. Common tunnel procedures such as those used with single bundle procedures are also possible for use with these methods.

At some point in the procedure prior to the use of the tensioning assembly, two tissue grafts are taken from the patient (autograft), such as from the ham strings or patellar tendon. Graft material can also be obtained from a donor tissue bank (allograft) or from a ligament manufacturer (synthetic). The grafts will have a securing end and a tensioning end or they can be folder over themselves to create the securing and tensioning ends. The first graft attachment sutures are attached to the tensioning end of the first tissue strand and second graft attachment sutures are attached to the tensioning end of the second tissue strand. This attachment can be of known methods to include woven sutures. In some embodiments, the tissue graft is pre-conditioned prior to placement in the patient's tunnels. This pre-conditioning is performed using common methods that include but are not limited to using a graft board that puts a stress of about 20 to 45 pounds on the graft for a period of 10 to 40 minutes or preferably about 20 minutes.

The tissue graft is then placed through the tunnels bored through the tibia and femur. This placement can be made using any common surgical techniques to include placing the end of the tissue graft opposite the sutures, the securing end, through the tunnels bored through the tibia and femur thereby pulling the ligament tissue into its femoral attachment area. At this area then, the securing end of the graft is fixed with the surgeon's fixation device of choice. The tensioning sutures and a portion of the graft extend out of an access portal in the patient's leg near the portal in the tibia.

As shown in FIG. 6, one embodiment of the methods of using the surgical tensioning assembly starts at Step 605 and is followed by Step 610 which comprises ensuring the first end, the securing end, of the tissue graft is secured in the bone tunnel.

With Step 615, the surgical tensioning assembly is affixed to the surgical location. A surgical tensioning assembly capable of applying tension to each of the tissue grafts is provided, an example of which is the tensioning assembly described more fully herein. At some point prior to affixing the assembly, the guide pins are affixed to the surgical area. Preferably this is done after the tunnels are drilled. In one embodiment, the guide pins are placed using a drill guide similar the those described above and the guide pins are drilled into the bone or are otherwise affixed to the surgical area as guided by the drill guide. The surgical tensioning assembly is then temporarily fixed near the tibial tunnel site of an ACL or PCL ligament reconstruction by means of sliding the stabilization legs of the assembly over the guide pins.

Figure 8:
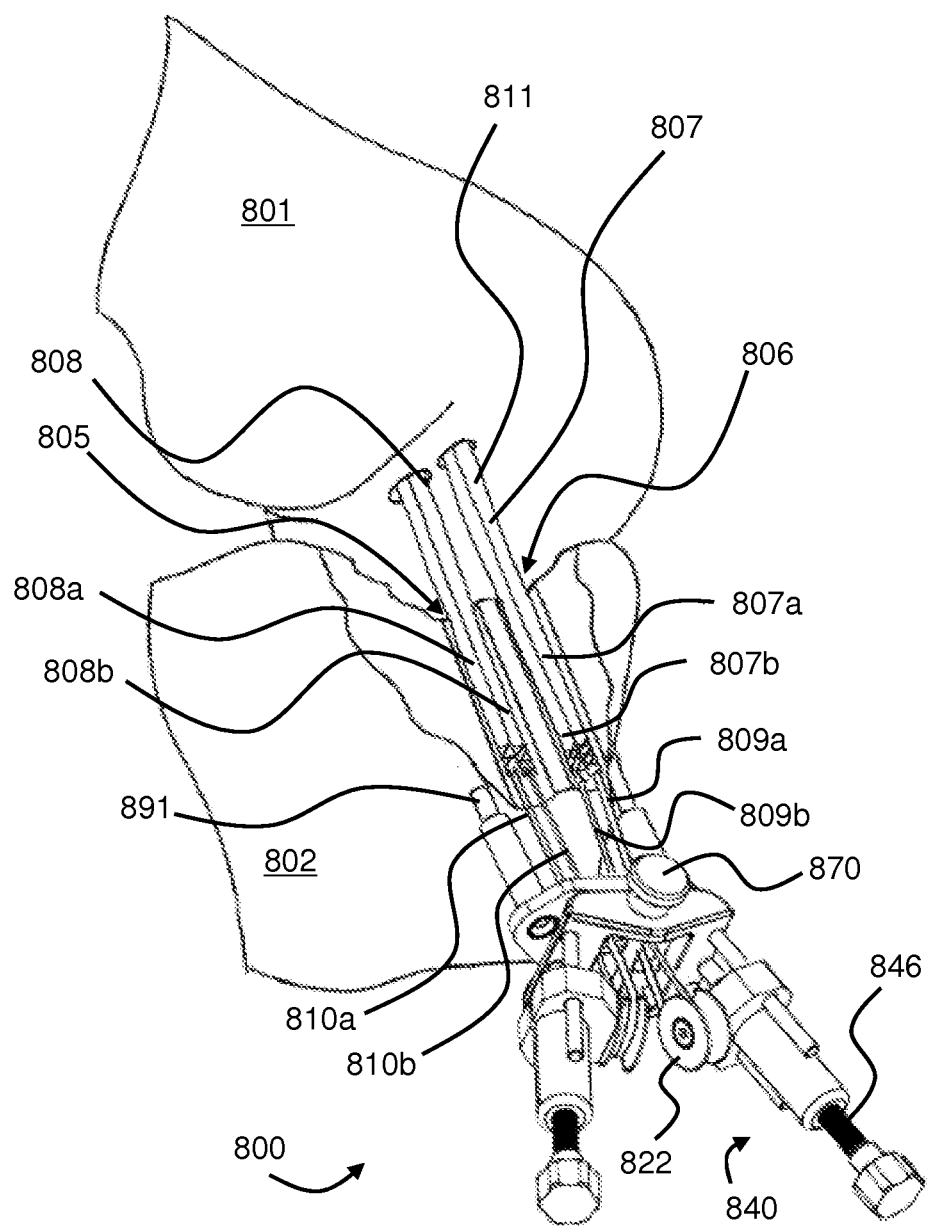
FIG. 8 is a side perspective view of a knee having one embodiment of the tensioning assembly affixed during an ACL reconstruction procedure, the figure showing a cut-away of the tibia illustrating placement of elements.

FIG. 8 illustrates the use of one embodiment of the assembly at the point of attachment on a tibia for a double-bundle ACL reconstruction. As shown, the tensioning assembly 800 is affixed to the tibia 802 by two mounting pins 892 received in the stabilization legs 891 of the assembly. The tissue graft 811 in this embodiment comprises two strands 807 and 808 that have been doubled over upon each other to create two double bundle strands having two legs each on the tibial side that are able to be secured in the tibial tunnel. Elements 807a and 807b represent the two tensioning legs of strand 807 and elements 808a and 808b represent the two tensioning arms of strand 808. As shown, each of the arms are attached to a suture and positioned in the tibial tunnels 805 and 806. The sutures may be woven or otherwise secured to the arm of the strand and the free ends of the sutures are passed out of the tunnel, through the tensioning assembly.

With Step 615, the second, tensioning end of the tissue is engaged with the engagement elements. This is done by taking the sutures that are associated with the tissue grafts and pulling them through the gaps central to the tensioning assembly and engaging them with one variable force subassembly and attaching the other tissue strand to the other variable force subassembly. An engagement element is present on each side of the variable force subassembly such that two arms of the four-arm ligament can be attached to each variable force subassembly in a circular fashion. In the embodiment shown in FIG. 8, the two sutures 809a and 809b are attached to the arms 807a and 807b of strand 807 and are engaged with one of the engagement elements 822, here a pulley. Sutures 809a and 809b are looped around one pulley so that one arm suture is on one side of the pulley and the other arm suture is on the other side to balance forces between the two sutures. In this embodiment, the sutures are engaged further by tying the free end of the sutures to the other with a knot positioned close to the engagement elements. It is understood that any method of securing the sutures together can be used such as knots, clamps or other known methods. The sutures 810a and 810b of strand 808 are similarly engaged with the other pulley. By attaching two arms to each engagement element, those two arms will then see equal tension. If necessary, the adjustment elements 846 can be used to position the variable force assembly so that slack is taken out of the sutures.

After the sutures have been secured to the tensioning assembly, the assembly is used to apply a desired tensile load to each of the tissue graft strands with Step 630. This may be done, as illustrated in FIG. 8, by pulling the guide pin 870 so that the locking element allows the rocker arm to move freely and balance the forces on strands 807 and 808 as well as all four legs 807a, 807b, 808a and 808b. Then, by tightening the adjustment knobs of each variable force subassembly 840 described above, the force element is compressed and thereby applies a corresponding compressing force onto each engagement element 822 through the slide block. This force is essentially equal to the magnitude of the tensile load exerted by the force elements onto the tissue graft strand. And because the equalizing subassembly balances the force on the rocker arms, the force between the two variable force subassemblies is essentially equal.

The magnitude of compressive force exerted by the force element onto the slide block is essentially equivalent to the magnitude of the tensile force exerted onto the tissue graft by the engagement element. When the force element is a compressible material such as a spring, because the amount of compressive force exerted by a spring is directly related to the distance that the spring has been compressed, the compressive load exerted by the spring onto the slide block, and the tensile load exerted by the engagement element onto the tissue graft, can be indirectly measured by measuring the distance the spring has been compressed. Thus, the variable force subassembly may be equipped with a gauge or other means for measuring the magnitude of force so as to indirectly measure the amount of tensile load being exerted on the tissue graft during conditioning and pretensioning.

In the embodiment of the tensioning assembly in FIG. 1 and FIG. 8, ligament tension is read using a calibrated spring scale that measures and records the total tension on all four ligament arms. The magnitude of the tensile load being applied to each soft tissue strand may be measured by the displacement of the measuring element (452 in FIG. 4) relative to its respective slot (454 in FIG. 4) in the slide block, particularly by referencing the location of the measuring element in relation to corresponding markings on the side of the slide block as well known in the art and described above.

Step 635 comprises conditioning the tissue arm. With this step, the knee can then be cycled through a range of motion causing the tension to be redistributed between the four ligament arms. The process of varying the tensile load applied to each of the tissue graft strands by the tensioning device followed by cycling of the joint is repeated until a desired level of conditioning, pre-tensioning and associated joint stability and strength are achieved. The cycling assists in equalizing the stretching or movement of the tissue strands within the bone tunnels to more evenly nest and condition the strands.

Typical methods of conditioning strands of a single or multi-bundle ligament replacement are disclosed in U.S. Pat. No. 6,679,889 to West entitled "Apparatus and methods for independently conditioning and pretensioning a plurality of ligament grafts during joint repair surgery" which is herein incorporated in its entirety.

In one embodiment of the methods of this invention, the conditioning of the ligament with the tensioning assembly comprises cycling the joint while simultaneously monitoring the variations of the forces on the graft as shown by the tensioning assembly. In this embodiment, it is desirable to ensure that the variation between the lowest and the highest tension value through cycling is no more than about 15 percent or more preferably 10 percent. If this value is exceeded, the adjustment elements are adjusted to reduce the tension on the graft. Then, cycling is repeated while measuring the force variations. This process is repeated until a suitable force variation is witnessed. This force variation is used to ensure that the graft when fixed is not subjected to too much force.

When negligible losses in joint stability are observed, or when the proper tension values are obtained, Step 640 is performed which comprises securing the second end of the tissue graft to the bone by appropriate anchoring means known in the art. In one embodiment, the tissue is secured at the point of cycling where the greatest amount of tension is measured to minimize the possibility of "trapping" the knee. An example of anchoring means known in the art is intra-tunnel fixation with an interference screw, which is screwed directly into the hole in the patient's bone through which the tissue graft is passed by means of a driver. After the interference screw has been screwed in place, the driver is removed. Extra-tunnel fixation techniques are also suitable anchoring methods.

After the graft is anchored, the tensioning device is removed at Step 645. If guide pins are used to secure the tensioning device to the person's leg, these are also removed. The remaining portion of the soft tissue grafts that extend beyond the bone may be secured to the outer surface of the bone by securing means known in the art, such as a spiked washer, staple or post in order to reinforce fixation of the graft. The graft is then trimmed to remove the sutures, and any portals in the leg are closed.

The process is completed at Step 650.

It is understood that the operation of other embodiments, such as that illustrated in FIG. 5 is similar to the embodiment described above. When the assembly is positioned on the pins and the sutures are looped over the pulleys, an equalized and measured force can be applied to each of the sutures and the ligament arms connected to the sutures.

This ligament tensioning assembly and methods of use allow a surgeon to place the ligament under tension prior to fixation and allows them to observe the behavior of the new ligament as the knee is taken through a range of motion. This builds safety into the procedure so that the ligament is not over tensioned when secured in place and the knee entrapped, creating subsequent motion problems and/or arthritis.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

I claim:

1. A surgical tensioning assembly, said tensioning assembly comprising:
   an engagement subassembly having at least a first and second engagement element to engage at least two ligament arms;
   a means to vary a force applied to the at least two ligament arms through the engagement subassembly;
   a means to automatically balance the force applied to the at least two ligament arms so that when the at least two arms are engaged by the engagement elements, the force applied to the at least two ligament arms is balanced; and
   the means to automatically balance the force applied to the at least two ligament arms comprises a rocker arm operably connected to the means to vary a force so that the force applied to the at least two ligament arms is about equal.

2. The surgical tensioning assembly of claim 1 further comprising a means to removably attach the tensioning assembly to a patient's body.

3. The surgical tensioning assembly of claim 2 wherein the means to removably attach the tensioning assembly to a patient's body comprises a mounting subassembly having at least one stabilization leg to slidably attach to a guide pin affixed to the person's body whereby the tensioning assembly can be attached to and detached from the guide pin and the patient's body.

4. The surgical tensioning assembly of claim 1 wherein the at least two ligament arms are connected to at least one suture that engages the engagement elements.

5. The surgical tensioning assembly of claim 1 wherein the at least two ligament arms are connected to at least one suture that engages the engagement elements.

6. The surgical tensioning assembly of claim 1 wherein:
   the at least two ligament arms are connected to at least one suture; and
   the first and second engagement element comprises a first and second rotatable wheel configured to receive and retain the sutures when the sutures are connected and looped around the wheel.

7. The surgical tensioning assembly of claim 1 wherein the means to vary the force further comprises a variable force subassembly configured to apply a selective force to the first and second engagement elements.

8. The surgical tensioning assembly of claim 1 wherein the means to vary the force further comprises a first and second variable force subassembly configured to engage and apply a first and second selective force to the first and second engagement elements.

9. The surgical tensioning assembly of claim 1 wherein: the at least two ligament arms are connected to at least one suture;
   the engagement element comprises at least one rotatable wheel configured to receive and retain the at least one suture when the sutures are connected and looped around the wheel; and the means to vary the force further comprises a first and second variable force subassembly configured to apply and transfer a first and second selective force to the first and second engagement elements.

10. A surgical tensioning assembly, said tensioning assembly comprising: an engagement subassembly having a first and second engagement element capable of engaging at least two tissue arms; a variable force subassembly configured to engage and apply at least one selective force to the first and second engagement elements; and an equalizing subassembly operably connected to the variable force subassembly so that when the at least two tissue arms are engaged by the first and second engagement elements the force applied to the at least two tissue arms is balanced; and the equalizing subassembly comprising a rocker arm.

11. The surgical tensioning assembly of claim 10 wherein the engagement elements are capable of engaging at least two tissue arms.

12. The surgical tensioning assembly of claim 10 wherein the tissue arms are connected to at least one suture that engages the engagement elements.

13. The surgical tensioning assembly of claim 10 further comprising at least one stabilization leg configured to slidably receive a guide pin affixed to a person's body whereby the tensioning assembly can be attached to and detached from the guide pin and the person's body.

14. The surgical tensioning assembly of claim 10 wherein the variable force subassembly comprises no more than one force element.

15. The surgical tensioning assembly of claim 10 further comprising a mounting subassembly to removably attach the tensioning assembly to a person's body.

16. The surgical tensioning assembly of claim 10 wherein the equalizing subassembly further comprises:
   the rocker arm having a first and second end;
   a rocker mount; and
   a guide pin hingedly connecting the rocker mount to the rocker arm whereby a force on the first and second end of the rocker arm can be balanced.

17. The surgical tensioning assembly of claim 10 wherein:
   the variable force subassembly comprises a first and second force element; and
   the first force element adapted to transfer a first force to the first engagement element and the second force element adapted to transfer a second force to the second engagement element.

18. A surgical tensioning assembly, said tensioning assembly comprising:
   an engagement subassembly having a first and second engagement element capable of engaging at least two tissue arms;
   no more than one variable force subassembly configured to engage and apply a selective force to the first and second engagement elements;
   an equalizing subassembly operably connecting to the variable force subassembly about a pivot point such that when the at least two tissue arms are engaged by the first and second engagement elements the force applied to the at least two tissue arms is balanced about the pivot point; and
   the equalizing subassembly comprises a rocker arm operably connected to the means to vary a force so that the force applied to the at least two ligament arms is about equal.

19. A method for tensioning a multi-stranded soft tissue graft during joint repair surgery, said method comprising the steps of:
   affixing a surgical tensioning assembly to a patient's body;
   the surgical tensioning assembly comprising:
   an engagement subassembly having a first and second engagement element capable of engaging at least two tissue arms; a variable force subassembly configured to engage and apply at least one selective force to the first and second engagement elements; and an equalizing subassembly operably connected to the variable force subassembly so that when the at least two tissue arms are engaged by the first and second engagement elements the force applied to the at least two tissue arms is balanced; and the equalizing subassembly comprising a rocker arm; ensuring a first end of at least one tissue arm is secured in the patient's body; engaging a second end of the at least one tissue arms with the first and second engagement element of the tensioning assembly; applying a variable force to the first and second engagement element; and automatically equalizing the variable force between the first and second engagement element so that when at least one tissue arm is engaged by the first and second engagement element, the force applied by the engagement elements to the at least one arm is balanced.

20. The method of claim 19 wherein the step of engaging the second end of the at least one tissue arm is performed by at least two sutures connected to the second end the tissue arm.

21. The method of claim 19 wherein the step of engaging the second end of the at least one tissue arm comprises at least two tissue arms and each ligament arm being connected to a suture engaging the engagement elements.

22. The method of claim 19 wherein the step of automatically equalizing the variable force is performed by an equalizing subassembly.

23. The method of claim 19 wherein the method is used for tensioning a ligament during a ligament reconstruction of a patient's knee.

24. The method of claim 23 wherein the method further comprises:
   conditioning the ligament by cycling the patient's knee;
   measuring the variable force through the cycling and varying the variable force until a difference in the variable force does not exceed a difference of about 10 percent; and
   securing the second end of the ligament to the patient's knee.

* * * * *